United States Patent
Gell et al.

(10) Patent No.: US 6,465,713 B1
(45) Date of Patent: Oct. 15, 2002

(54) TAMPON HAVING AN APERTURED FILM COVER

(75) Inventors: Carol Gell, Belle Mead; Linda Pierson, Somerville; Mary Yeganeh, Piscataway, all of NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/097,555

(22) Filed: Jun. 15, 1998

Related U.S. Application Data (60) Provisional application No. 60/052,752, filed on Jun. 30, 1997.

(51) Int. Cl.[7] .................................................. A61F 13/15
(52) U.S. Cl. ................... 604/383; 604/385.18; 604/904
(58) Field of Search .................................. 604/904, 383, 604/363, 385.17, 385.18

(56) References Cited

U.S. PATENT DOCUMENTS

| | | | | |
|---|---|---|---|---|
| 1,932,383 A | * | 10/1933 | Richardson | 604/904 |
| 2,710,007 A | | 6/1955 | Greiner et al. | 128/263 |
| 3,340,874 A | | 9/1967 | Burgeni | 128/285 |
| 3,929,135 A | | 12/1975 | Thompson | 128/287 |
| 4,475,911 A | | 10/1984 | Gellert | 604/367 |
| 4,644,623 A | | 2/1987 | Raley et al. | 29/148.4 D |
| 4,710,186 A | | 12/1987 | DeRossett et al. | 604/383 |
| 4,863,450 A | | 9/1989 | Friese | 604/370 |
| 5,004,467 A | | 4/1991 | Hinzmann et al. | 604/904 |
| 5,374,258 A | * | 12/1994 | Lloyd et al. | 604/904 |
| 5,403,300 A | * | 4/1995 | Howarth | 604/904 |
| 5,567,376 A | * | 10/1996 | Turi et al. | 264/455 |
| 5,817,077 A | | 10/1998 | Foley et al. | 604/363 |

FOREIGN PATENT DOCUMENTS

| | | | | |
|---|---|---|---|---|
| EP | 0 113 958 A | | 7/1984 | |
| EP | 0 422 660 B1 | | 2/1994 | |
| GB | 2211096 | * | 6/1989 | 604/904 |
| WO | WO 91 10415 A | | 7/1991 | |
| WO | WO 94 04112 A | | 3/1994 | |
| WO | WO 97 09017 A | | 3/1997 | |

OTHER PUBLICATIONS

"Toxic Shock Syndrome", "Tampon Involvement in Menstrual TSS", Merlin Bergdoll (author), CRC press Inc., 1991, Chapter 10, pp. 187–221.*

* cited by examiner

*Primary Examiner*—Dennis Ruhl (57) ABSTRACT

An absorbent tampon has improved ease of insertion into and removal from a body cavity. This is accomplished by covering at least a portion of the outer surface of the tampon with an apertured polymeric formed film. The apertured formed film provides a smooth land area on the outermost surface of the tampon for gentle, nondrying passage along the vaginal walls. The apertures in the film allow fluid to pass through the cover and into the absorbent core, where the fluid is held to prevent leakage.

10 Claims, 5 Drawing Sheets

TAMPON HAVING AN APERTURED FILM COVER

This application claims the benefit of U.S. Provisional application No. 60/052,752, filed Jun. 30, 1997.

FIELD OF THE INVENTION

The present invention relates to a generally elongated tampon for insertion into a mammalian body cavity. These tampons have smooth, apertured polymeric formed film covers to provide for smooth gentle insertion into and removal from a body cavity.

BACKGROUND OF THE INVENTION

Catamenial tampons are used by women to absorb the flow of menstrual fluids to prevent leakage and staining of undergarments, and other clothing. Therefore, it is desirable for tampons to demonstrate good absorbency and to be able to absorb fluid quickly. Unfortunately, tampons are not without disadvantages and inconveniences. For example, tampons may unexpectedly leak if they do not expand quickly enough or fully enough to fill the vaginal canal. Tampons are also sometimes difficult or uncomfortable to insert into or remove from the vaginal canal. These insertion and removal difficulties may be especially apparent when the menstrual flow is light.

There have been many attempts to remedy these problems by altering the absorbent material or the outer cover of the tampon. Greener et al., U.S. Pat. No. 2,710,007, and Burgeni, U.S. Pat. No. 3,340,874, are examples of the use of low density material in portions of a tampon to promote rapid fluid absorption.

Gellert, U.S. Pat. No. 4,475,911, describes a tampon made up of an unbonded array of nonabsorbent, hydrophilic, resilient fibers completely enclosed within a porous overwrap of apertured formed film.

Thompson, U.S. Pat. No. 3,929,135, describes a topsheet useful in disposable absorptive devices, including catamenial tampons. The topsheet is an apertured formed film having tapered capillaries. The Examples in this reference describe a topsheet having a top surface which is more than about 90% open area.

Lloyd et al., U.S. Pat. No. 5,374,258, describes a tampon with a cover comprising lengthwise ribs. The ribs on the cover are parallel to the tampon's axis and are separated from one another by multiple transverse ribs. Howarth, U.S. Pat. No. 5,403,300, describes a tampon with a polymer net outer cover. The net comprises two intersecting sets of parallel ribs which are aligned obliquely with respect to the main axis of the tampon and to each other. The orientation of the ribs allegedly aids in the smooth insertion and removal of the tampon.

Commonly assigned, copending patent application to Foley et al., U.S. patent application Ser. No. 08/789,747 (also published as EP 685 215) describes a tampon which demonstrates low capillary suction pressure on the vaginal epithelium. The contents of this application are hereby incorporated herein by reference.

It is an object of this invention to provide a novel tampon with good absorbency and leakage protection, ease of insertion into and removal from a body cavity, and a relatively clean dry surface after use.

SUMMARY OF THE INVENTION

The tampons of this invention provide good absorbency and protection from leakage while providing a smooth surface for easy, gentle insertion into and removal from the vaginal canal. They accomplish this by providing a generally elongated absorbent core made from absorbent materials, and an outer cover made from an apertured formed film. The apertured polymeric formed film comprises a land region having a multiplicity of openings therein. Each of these openings is defined by a first aperture and sidewalls extending in a uniform direction from the first aperture. The side walls terminate in a second aperture. The open area formed cumulatively by the second apertures comprises less than about 35% of the surface area of the apertured polymeric formed film. The outer cover is oriented on the tampon such that the second apertures are adjacent the absorbent core.

The apertured formed film provides a generally smooth land area on the outermost surface of the tampon for gentle, nondrying passage along the vaginal walls. The apertures in the film allow fluid to pass through the cover and into the absorbent core, where the fluid is held to prevent leakage.

The tampon of the invention may be made by forming a generally elongated blank of absorbent material, attaching a length of apertured polymeric formed film so that it covers at least the generally elongated surface of the blank, and then compressing the covered blank to form a tampon. A withdrawal cord or string may be attached to the blank or the covered blank to aid a user in withdrawing the tampon from a body cavity after use.

DETAILED DESCRIPTION OF THE PREFERRED EMBODIMENT

Figure 1:
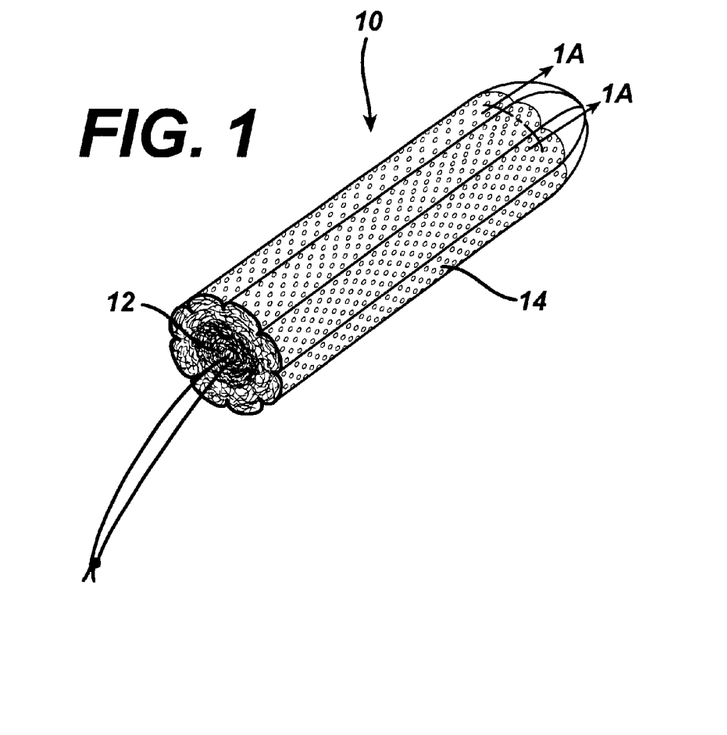
FIG. 1 illustrates a perspective view of a preferred embodiment of a tampon of the invention.
Figure 1A:
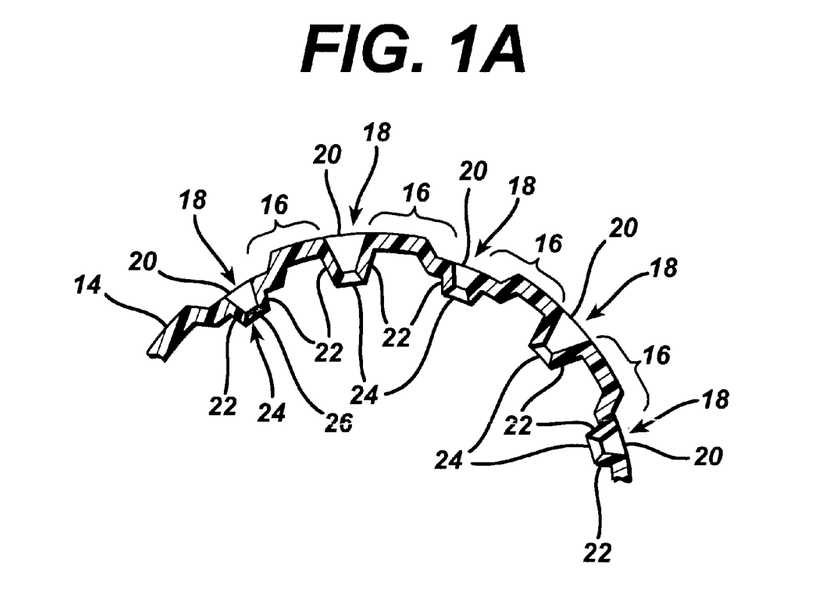
FIG. 1A illustrates an exploded cross-sectional view of the apertured film of FIG. 1.

As shown in FIGS. 1 and 1A, a preferred embodiment of the tampon 10 of the invention has a generally elongated absorbent core 12 of absorbent materials and an outer cover 14 of apertured formed film. The apertured formed film of the cover 14, when arranged in a substantially planar orientation, comprises a land region 16 having multiple openings 18 therein. Each opening 18 has a first aperture 20 in the land region 16 and side walls 22 extending therefrom in a substantially uniform direction and terminating in second apertures 24. It is not necessary that all of the second apertures 24 lie within the same plane.

Some of the second apertures 24 may be split by bridging fibrils 26 or thread-like extensions of the sidewalls across the second apertures 24. These fibrils 26 are created by incomplete aperturing of the starting film. An unexpected advantage of the fibrils 26 is that they provide the outer cover with additional capability for preventing absorbent core materials from protruding through the openings in the film.

This apertured formed film is placed on the tampon 10 so that the second apertures 24 are generally adjacent the absorbent core 12. An advantage of the apertured film cover is that it minimizes the presence of the absorbent materials on the surface of the tampon. The land region 16 has a projected land area which results from projecting the land region 16 onto a plane substantially parallel to it.

The size and number of the apertures in the film are chosen to minimize the penetration of absorbent core materials through the film. The presence of absorbent core materials on the surface of the tampon both increases friction against the vaginal wall upon insertion and contributes to desiccation of the vaginal wall during use, leading to removal discomfort. The absence of absorbent core materials on the surface of the tampon helps to maintain the ease of insertion and removal The length of the sidewalls connecting the first and second apertures may play a role in providing the tampon with improved insertion characteristics. The presence of the sidewalls between the first and second apertures imparts a generally three-dimensional quality to the film. This three-dimensional quality is in contrast to the generally two-dimensional quality of reticulated films such as that described in U.S. Pat. No. 4,710,186, the disclosure of which is herein incorporated by reference. Two-dimensional reticulated films more readily allow portions of the absorbent materials of the absorbent core to protrude through to the surface of the tampon.

The three-dimensional quality provided by the sidewalls helps to separate the absorbent materials of the absorbent core from the surface of the tampon. The longer the sidewalls, the greater the separation of the absorbent core materials from the tampon surface, and the less likely it is that the absorbent core materials will protrude through the openings in the apertured film to contact the vaginal tissues during insertion.

The optimum length of the sidewalls is dependent upon the type of absorbent material which is used for the absorbent core. Some types of absorbent materials may protrude more easily through the openings in the apertured film, and thus longer sidewalls may be required to prevent protrusion. It will be recognized by those familiar with the manufacture of tampons that tampons are often compressed during the manufacturing process. Such compression causes the sidewalls of the apertured film to fold over. Such folding, however, does not detract from the ability of the sidewalls to prevent protrusion of the absorbent materials through the openings in the apertured film.

Figure 2:
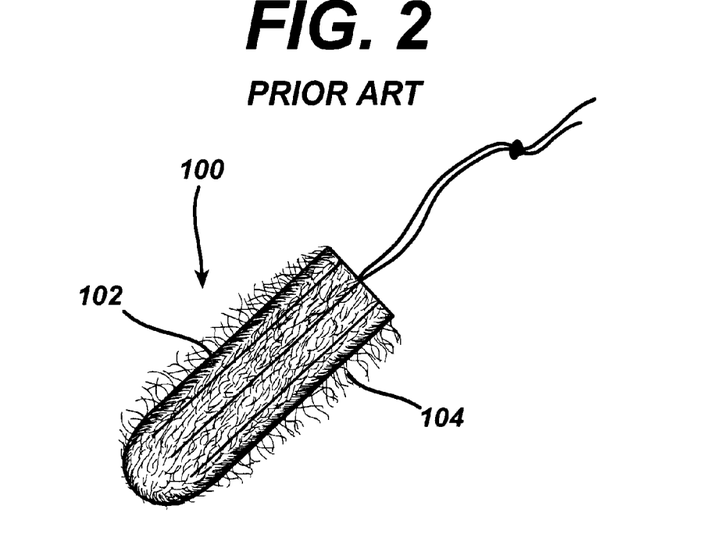
FIG. 2 is a side view of a tampon of the prior art with fibers protruding through the cover.

FIG. 2 illustrates a side view of a prior art tampon 100 with a fiber cover 102. The surface 104 of the prior art tampon 100 has a "fuzzy" appearance caused both by absorbent core fibers protruding through the fiber cover 102 and by loose fibers from the cover 102.

Figure 3:
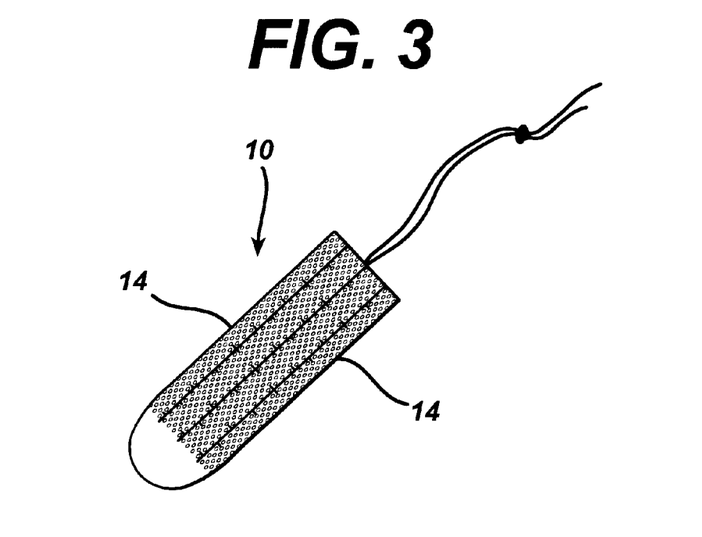
FIG. 3 is a side view of a tampon of this invention.

FIG. 3 shows a side view of a tampon 10 of the invention with an apertured film cover 14. The surface of the tampon 10 is smooth with the fibers substantially all contained by the cover 14. The apertured formed film cover 14 helps to hold the absorbent core fibers away from the surface of the tampon 10. Since the apertured formed film cover 14 does not comprise fibers, there are no loose cover fibers to interfere with insertion and removal comfort.

This smoothness may be measured by average surface roughness as measured by the Kawabata Surface Tester according to the method described in the Examples. Preferably, the average surface roughness is less than that of conventional fibrous tampon cover material. More preferably, the average surface roughness is less than about 3 microns.

The absorbent core of the tampon may comprise any absorbent material, including but not limited to cellulosic fibers such as rayon and cotton, other natural or synthetic absorbent fibers, superabsorbent fibers, absorbent foams, absorbent gelling agents, and the like. In a preferred embodiment, the absorbent core of the tampon comprises a blend of rayon and cotton.

The apertured formed film of the invention may comprise any polymeric film-forming material including but not limited to polyethylene, polypropylene, other polyolefins, ethylene vinyl acetate, polyesters, polystyrene, polyamides, polyethers, copolymers of these, and blends of these. In a preferred embodiment, the apertured formed film of the invention comprises a blend of ethylene vinyl acetate and polypropylene. In another preferred embodiment, the apertured formed film comprises a blend of polypropylene and low density polyethylene.

The generally elongated absorbent core has a generally elongated surface and two end surfaces. Preferably, the apertured formed film substantially covers at least the generally elongated surface of the absorbent core to form an outer cover on the tampon. The outer cover is oriented and configured such that the second apertures are adjacent to the absorbent core. One or both of the ends of the absorbent core may also be covered, but this is not necessary to obtain the insertion and removal advantages of the invention.

The land region of the apertured formed film is chosen such that it provides the outer body-contacting exterior of the tampon with a gliding surface which allows for smooth and easy insertion of the tampon into a body cavity. The smoothness of the surface allows the tampon to slide easily over the vaginal tissues, thereby reducing the frictional drag which may occur when fibrous or absorbent or less smooth tampon surfaces rub along the sensitive vaginal tissues. The projected land area, projected side wall area, and open area of a given area of apertured formed film are equal to unity. Of these three areas, the easiest to determine is the open area. It has been found that apertured formed films with open area of less than about 35% function effectively to provide this smooth surface on tampons. However, apertured films with open area of as little as 2% are also effective on such tampons.

Open area may be determined by using image analysis to measure the relative percentages of apertured and unapertured, or land, areas. Essentially image analysis converts an optical image from a light microscope into an electronic signal suitable for processing. An electronic beam scans the image, line-by-line. As each line is scanned, an output signal changes according to illumination. White areas produce a relatively high voltage and black areas a relatively low voltage. An image of the apertured formed film is produced and, in that image, the holes are white, while the solid areas of thermoplastic material are at various levels of gray.

The more dense the solid area, the darker the gray area produced. Each line of the image that is measured is divided into sampling points or pixels. The following equipment can be used to carry out the analysis described above: a Quantimet Q520 Image Analyzer (with v. 5.02B software and Grey Store Option), sold by LEICA/Cambridge Instruments Ltd., in conjunction with an Olympus SZH Microscope with a transmitted light base, a plan 1.0× objective, and a 2.50× eyepiece. The image can be produced with a DAGE MTI CCD72 video camera.

A representative piece of each material to be analyzed is placed on the microscope stage and sharply imaged on the video screen at a microscope zoom setting of 10×. The open area is determined from field measurements of representative areas. The Quantimet program output reports mean value and standard deviation for each sample.

Figure 4:
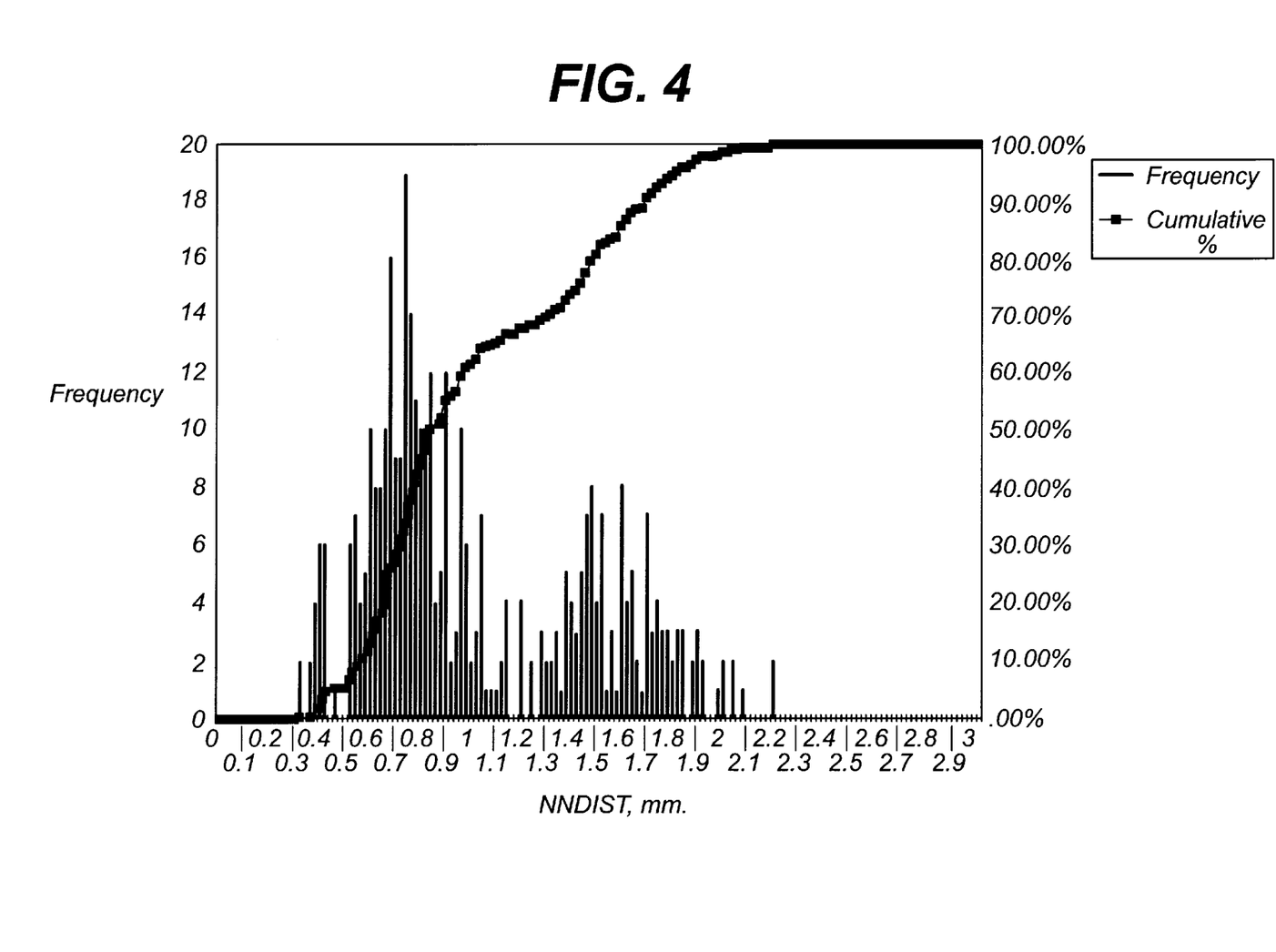
FIG. 4 is a graph illustrating the frequency of the distances of "Nearest Neighbor" apertures ("NNDIST") in a preferred embodiment of an outer cover for the tampon of the invention.
Figure 5:
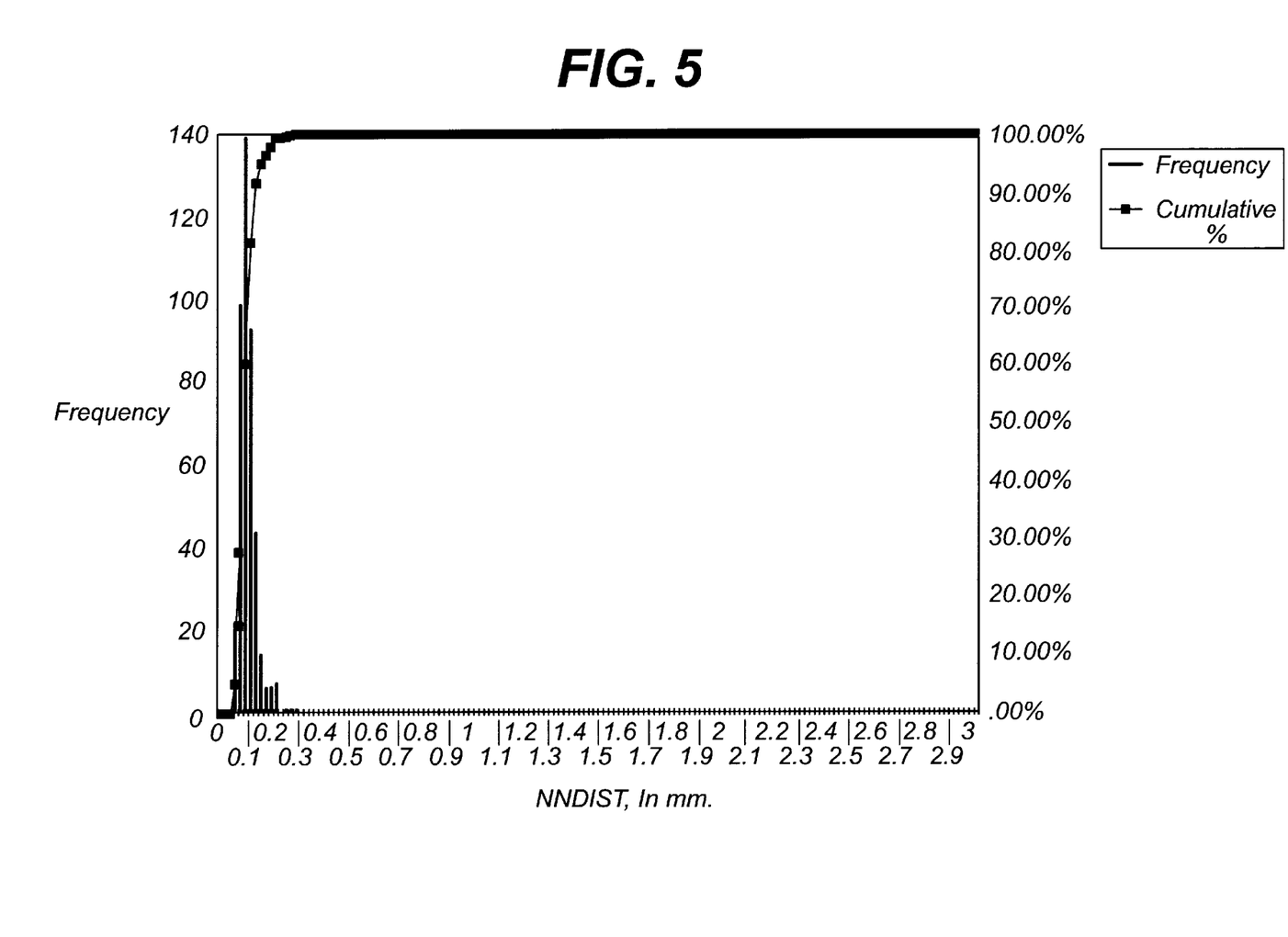
FIG. 5 is a graph illustrating the frequency of the distances of "Nearest Neighbor" apertures ("NNDIST") in a fibrous cover for a commercially available o.b.® tampon.

In addition to open area, the apertured formed film of the tampon of the invention is characterized by a distribution of the distances of nearest neighbor apertures. Nearest neighbor distance may be determined by a variety of means including the use of image analysis for the calculation of the "nearest neighbor" in an array of apertures. The nearest neighbor distance is the distance between an aperture and the aperture which is its nearest neighbor in an apertured formed film, measured from the centroid of the first aperture to the centroid of its nearest neighbor. This distance, when plotted against the frequency of such distances, provides a frequency distribution of nearest neighbors for the apertures in the film. Such a nearest neighbor distribution may be observed in FIGS. 4 (an apertured formed film according to the present invention) and 5 (a thermobonded fibrous web). It can be noted from FIG. 4 that the distribution for this apertured formed film sample is binodal; that is, there is a first distribution of nearest neighbor distances in the 0.5 to 1.1 mm range and a second distribution in the 1.1 to 2.5 mm range. This binodal distribution is attributed to the presence of fibrils across about 60% of the second apertures in this sample of apertured formed film. In contrast, as shown in FIG. 5, the nearest neighbor distribution for a fibrous nonwoven cover similar to that formed on a commercially available o.b.® tampon shows a very narrow distribution of nearest neighbor distances. Additionally, the nearest neighbor distances for the fibrous cover are much smaller than for the film cover. This illustrates that the apertures in the fibrous cover are much closer together than the apertures in the film.

The apertured formed film may be applied as an outer cover to an absorbent core to form a tampon by any of a number of known methods. Preferred methods of applying the cover are disclosed in U.S. Pat. No. 4,863,450 (Friese), in which a length of cover is attached to one end of a length of absorbent material and the assembly is rolled up into a cylinder such that the cover forms the outside surface of the cylinder, and U.S. Pat. No. 5,004,467 (Hinzmann et al.), in which one end of an absorbent cylinder is placed in the center of a rectangle of cover, and the cover is folded up and around the sides of the cylinder.

The contents of these two patents are hereby incorporated herein by reference.

After the cover is applied to the absorbent core, the covered core is radially compressed, to form a tampon pledget. A preferred compressed tampon and method for making it are described in commonly assigned, co-pending U.S. patent application Ser. No. 07/596,456 (Friese et al.), the contents of which are hereby incorporated herein by reference. The tampon of Friese et al. has a generally cylindrical shape formed by multiple longitudinal, relatively low-density ribs surrounding a more highly compressed core. The term "generally elongated" as used herein is intended to include the generally cylindrical tampon of Friese et al. as well as other tampons with a generally elongated shape.

The compressed pledget may be inserted into a user's body cavity with the user's fingers (digitally) or by means of an applicator.

Figure 6:
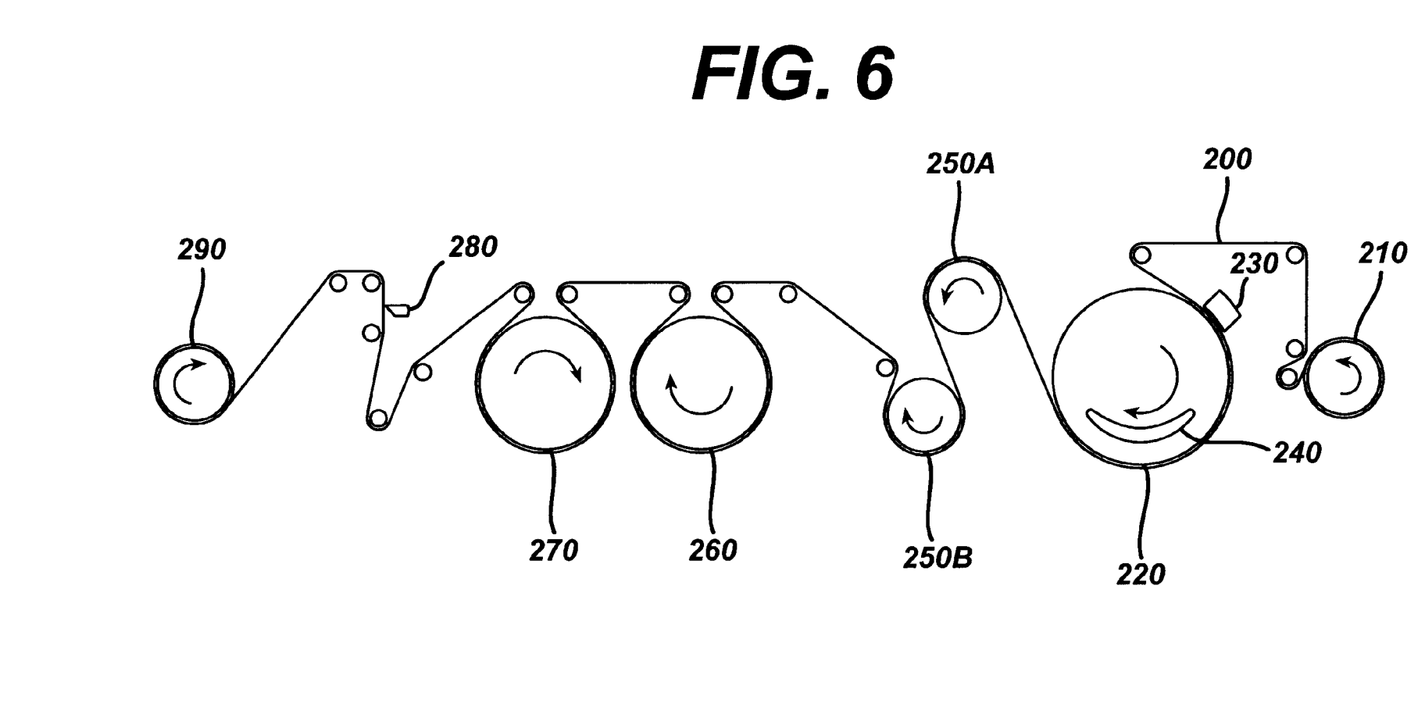
FIG. 6 is a diagrammatic view of a preferred type of apparatus for producing apertured formed film for use on the tampon of the present invention.

Apertured polymeric formed films are known and may be made by a number of methods which are known to those in the art, including hot air aperturing and water aperturing. A preferred apertured formed film for this invention is made using an apparatus as described in U.S. Pat. No. 5,567,376, the contents of which are hereby incorporated herein by reference. FIG. 6 illustrates a method of making an embodiment of an apertured film for use in this invention. A continuous starting film 200 is unwound from an unwind station 210 and supported on a three-dimensional apertured forming member 220. Situated above the starting film 200 is a manifold 230 for applying multiple fine streams of hot water to the upper surface of the starting film 200 as the film, supported on the forming member 220, passes under the manifold 230. The water may be applied at varying pressures. High pressures (i.e., 900 pounds per square inch) or low pressures (i.e., 165 pounds per square inch) may be used, as may combinations of high and low pressures. Disposed beneath the forming member 220 is a vacuum manifold 240 for removing water which is directed onto the upper surface of the starting film 200 as it passes under the manifold 230.

The pressurized streams of hot water cause the film to conform to the topography of the apertured forming member 220 and to rupture in the areas where the film overlies the apertures in the forming member 220. The resulting apertured formed film has a top surface corresponding to the surface contacted by the water streams, and a bottom surface corresponding to the surface supported by the forming member 220. The apertured film is then passed through one pair or dewatering rolls, 250A and 250B, and one pair of backing rolls, 260 and 270, to remove excess water and to dry the film. Surfactant is then applied to the top surface of the apertured film, the film is slit, e.g., by a cutting knife 280, into appropriate widths for tampon converting lines, and the narrow widths of film are wound onto standard cores 290.

The narrow widths of apertured formed film are then cut into strips of predetermined lengths. The cut edge of each strip of the apertured film is heat-welded to the outside of the rear end of a section of a cotton/rayon nonwoven ribbon. The blend of cotton and rayon in the nonwoven ribbon may range from 100% cotton and 0% rayon to 0% cotton and 100% rayon. Preferably, the blend of cotton to rayon ranges from 25:75 to 0:100. The nonwoven ribbon is provided with a withdrawal cord and rolled up on itself to form a tampon blank so that the apertured film length extends over the circumference of the tampon blank with the top surface of the apertured film facing away from the nonwoven ribbon. The free end of the apertured film length is heat-sealed onto the outer apertured film-covered surface of the blank. The blank is subsequently radially compressed to produce the final form of the tampon.

EXAMPLES 1A, B, C, D

Tampons 1A and 1C are made by applying the apertured film cover according to the method above. Tampons 1B and 1D are made by first rolling up a section of a cotton/rayon nonwoven ribbon to form a generally cylindrical tampon blank. One end of the blank is placed on the center of a length of apertured film. The apertured film is folded up and around the sides, or generally cylindrical surface, of the tampon blank. The covered blank is then radially compressed to form a tampon.

Tampons 1A, 1B, 1C, and 1D are tested for absorbency by a standard Syngina test, as described in the Federal Register, Part III, Department of Health and Human Services, Food and Drug Administration (21 CFR Part 801, pp. 37263–4, Sep. 23, 1988). It can be seen from Table 1 below that tampons made with films of small open area (high land area)

demonstrate Syngina capacities which are comparable with tampons made with higher open area (lower land area) films and fibrous covers.

TABLE 1

| Product | Apertured Film Open Area (%) | Syngina Capacity (g) |
| --- | --- | --- |
| Tampon 1A with apertured film cover | 2.3 | 9.2 |
| Tampon 1B with apertured film cover | 3.0 | 9.5 |
| Tampon 1C with apertured film cover | 3.6 | 9.3 |
| Tampon 1D with apertured film cover | 22.7 | 9.7 |
| Commercial o.b. ® with fibrous cover | — | 9.2 |

EXAMPLE 2

A comparison was made of the perceived insertion and removal comfort of two control products, (1) a super absorbency commercial digital tampon with a fiber cover (o.b.® Brand), and (2) a digital tampon made with a two-dimensional reticulated film, such as that described in U.S. Pat. No. 4,710,186, and an experimental tampon made by substituting an apertured film cover with an open area of 3% for the fiber cover on a super absorbency commercial o.b.® tampon. The test tampon (Example 2) was made according to the same method used to made Tampons 1A and 1C above. Fifty-five panelists were each given one each of the control product and the test tampon. Each participant was instructed to insert the tampons digitally during nonmenstrual days only to simulate light flow days. Each tampon was to be worn for 3 to 4 hours before being removed, and there was to be a minimum of 20 hours between the testing of each tampon. The panelists completed questionnaires immediately after the insertion process of each tampon and then again immediately after the withdrawal process of each tampon. The panelists were asked to rate each tampon from 0, extreme negative, to 10, extreme positive, on their perceptions of various attributes of the tampons. The results of the test are shown below in Table 2.

TABLE 2

| Attribute | o.b. ® Super absorbency | Reticulated Film of U.S. Pat. No. 4,710,186 | Example 2 Tampon |
| --- | --- | --- | --- |
| Overall insertion performance | 6.9* | 7.4 | 7.7 |
| Easy to position for insertion | 7.1* | 7.7 | 7.9 |
| Comfortable during insertion | 7.1* | 7.6* | 8.1 |
| Easy glide | 6.4* | 7.3 | 7.7 |
| Overall removal | 6.7* | 7.2 | 7.4 |

*Indicates that the number shown is significantly less at a 95% confidence level as measured by the Paired T-test.

It can be seen from the results in Table 2 that the tampon with the apertured formed film cover (Example 2 tampon) was rated higher than the commercial tampon for overall insertion, ease and comfort of insertion, easy glide, and overall removal.

These cover materials were also tested for Coefficient of Friction on polished steel and surface roughness. The surface roughness was measured using the Kawabata Surface Tester KES-FB-4, available from Kato Tekko (Kyoto, Japan).

The Kawabata Surface Tester allows the measurement of surface roughness of films and nonwoven fabrics. In performing this test, the mean deviation of surface roughness, SMD, is measured over a distance of 2 cm. The contactor for measurement of surface roughness is a steel piano wire (0.5 mm diameter, 5 mm length) placed on the material surface with a contact force of 10 gf (gram force). The contactor is specially designed to simulate the human finger surface. The specimen is moved between a 2 cm interval both backwards and forwards at a constant velocity of 0.1 cm/sec on a horizontal smooth steel plate. The tension of the specimen is kept constant at 20 gf/cm and the contactor stays in place during the measurement. The electrical signal related to the vertical displacement of the piano wire is then translated into a digital readout.

The results of the Kawabata Surface Tester and Coefficient of Friction on Steel are shown below in Table 3.

TABLE 3

| Product | Surface Roughness (microns) | Surf. Rough. Std. Dev. (microns) | Coefficient of Friction |
| --- | --- | --- | --- |
| Reticulated Film of U.S. Pat. No. 4,710,186 | 3.5 | 0.24 | 0.11 |
| Fibrous cover of Commercial o.b. ® | 3.2 | 0.20 | 0.16 |
| Apertured Formed Film as in Ex. 2 | 1.5 | 0.87 | 0.22 |

It can be seen from the surface roughness test results that the three-dimensional apertured formed film of the invention has a lower average surface roughness than either the fibrous cover from a commercial o.b.® tampon or a two-dimensional reticulated film. In the Kawabata Surface Roughness Test, lower measurements indicate lower surface roughness.

However, as Table 3 shows, the lower surface roughness does not result in a lower coefficient of friction. The apertured formed film has a higher coefficient of friction on polished steel than either the reticulated film or the fibrous cover. Surprisingly, a tampon surface that provides greater frictional drag demonstrates greater comfort upon actual insertion into and removal from a woman's vagina than a tampon having a cover with less frictional drag.

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. A tampon comprising a generally elongated absorbent core comprising absorbent material, and an outer cover comprising an apertured polymeric formed film, the apertured polymeric formed film comprising a land region having a multiplicity of openings therein; each said opening being defined by a first aperture and sidewalls extending in a substantially uniform direction from the first aperture and terminating in a second aperture, at least a portion of the second apertures being bridged by polymeric fibrils; and open area formed cumulatively by the second apertures comprising less than about 35% of the surface area of the apertured polymeric formed film; wherein the outer cover is oriented on the tampon such that the second apertures are adjacent the absorbent core.

2. The tampon of claim 1 wherein the absorbent core has at least one generally elongated surface, the outer cover being present over a substantial portion of the at least one generally elongated surface.

3. The tampon of claim 2 wherein the absorbent core has two end surfaces, at least one end surface being substantially covered by the outer cover.

4. The tampon of claim 1 wherein the absorbent core comprises absorbent fibers.

5. The tampon of claim 1 wherein the apertured polymeric formed film comprises a blend of ethylene-vinyl acetate and polypropylene.

6. The tampon of claim 1 wherein the apertured polymeric formed film comprises a blend of polypropylene and low density polyethylene.

7. The tampon of claim 1 wherein the absorbent core is generally cylindrical.

8. The tampon of claim wherein the open area comprises about 2% to about 35% of the surface area of the apertured polymeric formed film.

9. The tampon of claim 8 wherein the open area comprises about 2% to about 25% of the surface area of the apertured polymeric formed film.

10. The tampon of claim 1 wherein at least 50% of the second apertures are bridged by polymeric fibrils.

* * * * *